United States Patent [19]

Wardlaw

[11] Patent Number: 5,776,078

[45] Date of Patent: Jul. 7, 1998

[54] CASSETTE HOLDER FOR CAPILLARY TUBE BLOOD TESTING WITH INTEGRAL SEALING MEANS

[75] Inventor: Stephen C. Wardlaw, Old Saybrook, Conn.

[73] Assignee: Robert A. Levine, Guilford, Conn.

[21] Appl. No.: 755,363

[22] Filed: Nov. 25, 1996

[51] Int. Cl.⁶ .................................................. A61B 5/14
[52] U.S. Cl. .................................................. 600/576
[58] Field of Search .......................... 128/763, 770, 128/771; 604/192, 196–198

[56] References Cited

U.S. PATENT DOCUMENTS

| | | |
|---|---|---|
| 4,024,857 | 5/1977 | Blecher et al. ............... 128/763 |
| 4,215,700 | 8/1980 | Crouther et al. ............. 128/763 |
| 4,805,635 | 2/1989 | Korf et al. .................... 128/763 |
| 5,257,984 | 11/1993 | Kelley ......................... 128/763 |

*Primary Examiner*—Max Hindenburg
*Attorney, Agent, or Firm*—William W. Jones

[57] ABSTRACT

A transparent capillary tube is held in a cassette-type container during blood drawing and blood testing procedures. The cassette protects the capillary tube against breakage; allows the placement of patient and blood sample testing information labels thereon; and allows technicians to draw and test blood samples without having to come into direct contact with the capillary tube, or the blood. Once the blood sample is drawn into the capillary tube, the cassette can be used in the performance of kinetic gravimetric blood cell counts.

13 Claims, 2 Drawing Sheets

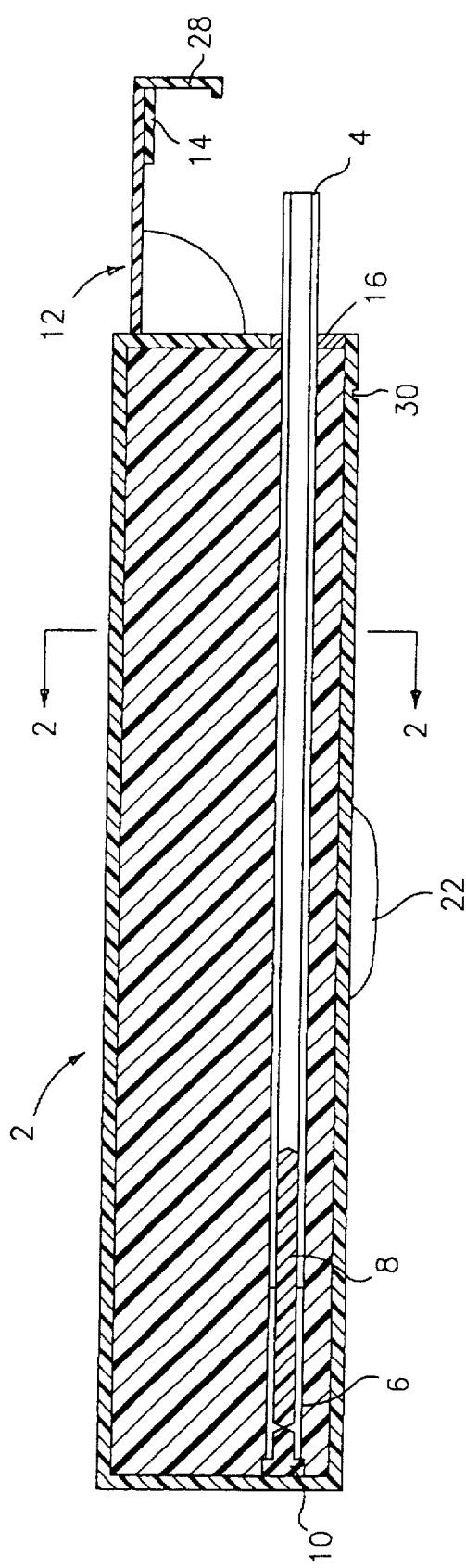
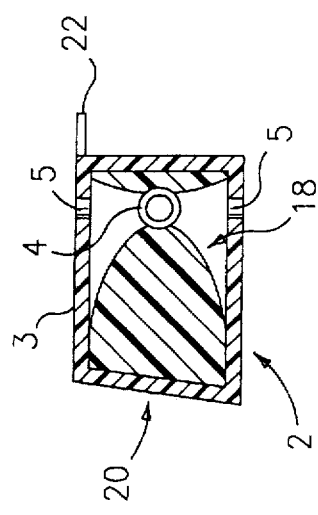
FIG. 1
FIG. 2

CASSETTE HOLDER FOR CAPILLARY TUBE BLOOD TESTING WITH INTEGRAL SEALING MEANS

TECHNICAL FIELD

This invention relates to a cassette for holding a transparent blood sampling tube during drawing of a blood sample and during gravimetric analysis of the blood sample. More particularly, this invention relates to a cassette which allows drawing and analysis of blood samples without exposing technicians who are drawing and analyzing the blood sample to direct contact with the sampling tube or the blood sample.

BACKGROUND ART

Glass capillary tubes are used as vessels for obtaining and testing blood samples in a variety of situations. Specifically, glass capillary tubes are used in the performance of hematologic tests, such as those described in U.S. Pat. No. 4,027,660 granted Jun. 7, 1977 to S. C. Wardlaw et al. Although the use of such tubes is widespread in connection with the performance of various blood tests, there is an increasing reluctance on the part of technicians and others using these tubes, because of the risk of tube breakage and technician exposure to potentially infectious blood. The glass tubes are, however, necessary for many tests, particularly in those cited above, and there is no ready alternative blood container. Plastic, or plastic coated tubes have been used in some circumstances in an effort to reduce the risk of breakage, but tube breakage is only marginally reduced, and the problem of contaminated blood contact still remains. The danger from the tubes remains even after the tests are performed, and the tubes must be disposed of in the same manner as hypodermic needles. An additional problem with capillary tube collections is that there is no place on the tube where one can place a label. Thus, the contents of the tube must be processed immediately, or the tube must be placed into a separate, labeled container.

In normal use, blood is drawn into one end of the tube by means of capillary action or by means of a pipette. Once filled, the tube is wiped, capped, and then may be placed into an instrument or may be transported. The risk of collecting blood in a capillary tube arises from several features inherent in its design. First, the tube, because of its small diameter, is easily broken if mishandled. The steps of wiping, and especially capping, can generate bending pressures which can shatter the tube and injure the operator. The small size of the tube accentuates this danger because it is clumsy to handle, especially when wearing rubber gloves. The wiping is necessary because the blood that accumulates on the side of the tube during its filling will contaminate the surroundings if not removed, but this removal directly exposes the operator to the blood. It would be desirable to be able to continue to use glass capillary tubes for drawing and testing blood without exposing one to broken glass or blood. All of the aforesaid drawbacks can be overcome by the instant invention, which relates to a special cassette in which the capillary tube is contained.

DISCLOSURE OF THE INVENTION

This invention relates to a special cartridge or cassette which is preloaded with a capillary tube and may have a blood cell layer-elongating float insert, of the type described in the aforesaid prior art. The cassette may be factory preloaded so that the medical technician or the like handling the cassette will not experience direct contact with the tube. The cassette contains an internal recess having a closed end and an open end. A tube closure plug is positioned in the closed end of the cassette recess, and the float is positioned in the cassette recess in abutment with the closure plug. During assembly, a capillary tube containing appropriate dyes and anticoagulant reagents is inserted into the cassette recess by way of the open end thereof to an extent necessary to cause one end of the capillary tube to telescope over one end of the float in the cassette recess when a float is included in the assembly. This degree of tube insertion will result in a portion of the capillary tube protruding from the open end of the cassette recess.

To draw a blood sample, the technician can grasp the cassette and use the protruding end of the capillary tube to draw the sample, as by means of a finger stick or the like. When the sample is drawn, the technician can slide the tube fully into the cassette recess without having to personally touch the tube. Once the tube and its contents are fully contained within the cassette, the cassette can be labeled with patient and desired test information, and the necessary blood tests can be performed. The blood tests may be performed by means of a kinetic reading and analyzing procedure and instrument which are described in co-pending applications Attorney's Docket Nos. H-1274, and H-1219 respectively.

It is therefore an object of this invention to make the use of blood sampling capillary tubes less risky for the user while retaining the advantages of capillary tubes as a blood sampling and testing vehicle.

It is a further object of this invention to provide a capillary tube holder which enables one to draw a sample of a patient's blood without the need for the person drawing the blood sample to come into direct contact with the capillary tube, or the blood.

It is an additional object of this invention to provide a capillary tube holder of the character described which protects the capillary tube against breakage.

It is another object of this invention to provide a capillary tube holder of the character described which provides sufficient surface area to conveniently accommodate the securement of a patient and/or blood test information label.

These and other objects and advantages of the invention will become more readily apparent from the following detailed description of the invention when taken in conjunction with the accompanying drawings, in which:

BRIEF DESCRIPTION OF THE DRAWINGS

FIG. 1 is a longitudinal cross-sectional view of a preferred embodiment of a capillary tube and tube-holder cassette assembly formed in accordance with this invention.

FIG. 2 is a cross-sectional view of the cassette and tube assembly taken along line 2—2 of FIG. 1;

BEST MODE FOR CARRYING OUT THE INVENTION

Figure 4:
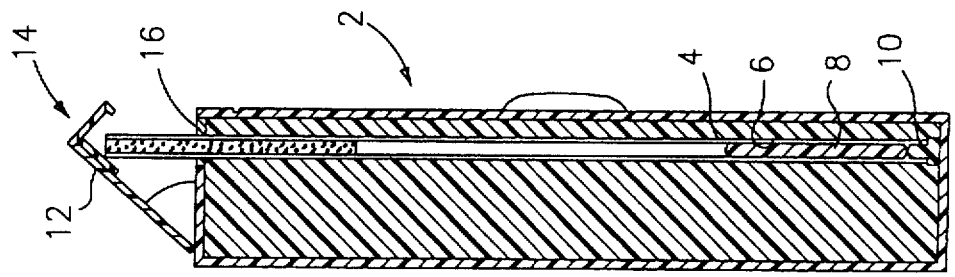
FIG. 4 is a longitudinal cross-sectional view of the cassette and tube assembly after the tube has been filled with blood.

Referring now to FIG. 1, the body of the cassette 2 is generally rectangular and preferably formed from injection molded plastic such as polystyrene. The outside dimensions are approximately 1.0 cm×1.5 cm×8.5 cm. A glass or plastic capillary tube 4 is positioned within a recess 6 in the cassette and is longitudinally movable therein. When blood tests are to be performed in accordance with the teachings of the previously cited U.S. Pat. No. 4,027,660, a plastic float 8 may also be contained partially within the tube 4 and the cassette recess 6. An elastomeric plug 10 is positioned at the closed end of the recess 6 so as to engage the end of tube 4 when the cassette 2 is closed and the tube 4 is fully inserted into the cassette 2. Alternatively, the plug 10 may be omitted, and a self-sealing capillary tube having a hygroscopic seal may be used. At the open end of the cassette 2 is a hinged lid 12, having an elastomeric pad 14. Both the elastomeric plug 10 and the pad 14 may be made from any convenient elastomer, and are preferably made of silicone. Also, at the open end of the cassette 2 is an absorbent gasket 16 which may be fabricated from a hydrophilic paper, foam or the like, and which surrounds the tube 4. The gasket 16 also bears against the tube 4 and prevents the tube 4 from freely sliding in the recess 6. The lid 12 preferealby is provided with a flange 28 which engages a notch 30 in the side of the cassette 2 to lock the lid 12 in a closed position.

FIG. 2 shows the internal structure of the cassette 2 which forms the recess 6. Inside of the cassette 2 are a pair of opposed supports 18 which laterally constrain the tube 4. The supports 18 are positioned so that at least one side of the tube 4 is visible from the outside of the cassette 2 through a slot 5 or a transparent window contained in a wall 3 of the cassette 2. To ensure correct positioning of the cassette 2 in a centrifuge-reader instrument, such as that described in co-pending patent application Attorney's Docket No. H-1219, one side 20 of cassette 2 may be tapered or otherwise configured so the cassette can be dovetailed into a matching slot in the centrifuge-reader instrument; and a tab 22 may be included in order to facilitate the insertion and removal of the cassette 2 into and out of the centrifuge-reader slot.

Figure 3:
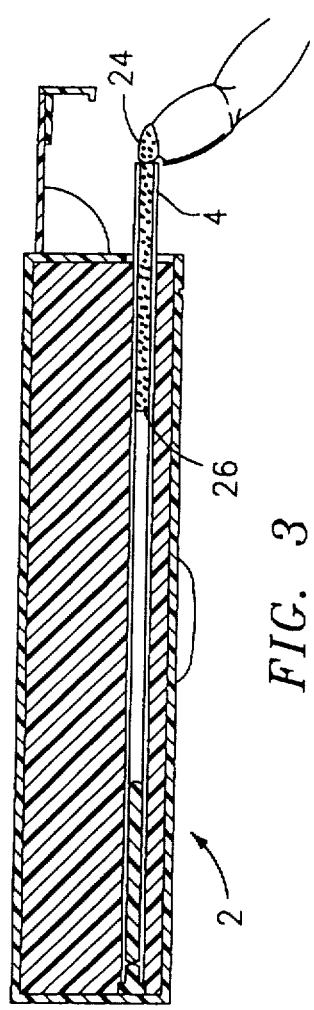
FIG. 3 is a longitudinal cross-sectional view of the cassette and tube assembly as it is being filled.

As seen in FIG. 3, when a drop of blood 24 from a finger puncture, or other source of blood, is brought into contact with tube 4, the blood will be drawn into the tube 4 by capillary action. The flow of blood may be halted by the operator withdrawing the tube 4 away from the blood drop 24, or by providing a hydrophobic region 26 in the tube 4 which negates the capillary forces acting on the blood in the tube 4. For most tests, the blood sample may be anticoagulated by a thin coating of heparin within the tube 4.

As noted in FIG. 4, the cassette lid 12 is pivoted in a closing direction thus causing the pad 14 to bear upon the end of tube 4. As the lid 12 is closed, the tube 4 is pushed completely into the cassette recess 6 until the inner end of the tube 4 engages the plug 10 so that the inner end of the tube 4 is sealed by the plug 10. As the tube 4 passes into the cassette 2, the tube 4 will be wiped by the absorbent gasket 16 so as to remove all excess blood from the outside of the tube 4.

Figure 5:
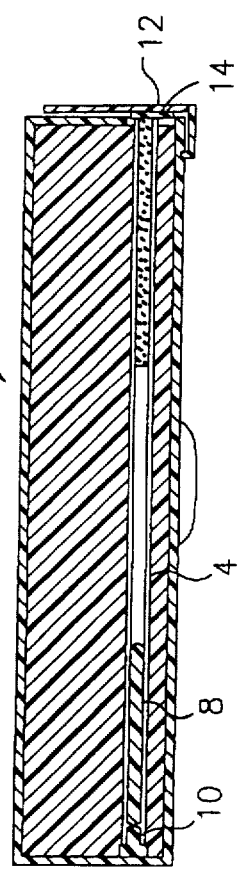
FIG. 5 is a longitudinal cross-sectional view of the cassette and tube assembly after the cassette has been completely closed.

As illustrated in FIG. 5, the elastomeric properties of the plug 10 and the pad 14 will keep the top end of the tube 4 pressed tightly against the pad 14 thereby closing the top end of the tube 4, while the plug 10 seals the bottom end of the tube 4. The tube-cassette assembly illustrated in FIG. 5 is placed in a centrifuge assembly of the type described in co-pending U.S. patent application Ser. No. 08/814,536, filed Mar. 10, 1997 wherein the cassette and tube assembly are centrifuged, and the blood constituent measurements are made in accordance with the kinetic method described in co-pending U.S. patent application Ser. No. 08/814,535, filed Mar. 10, 1997.

It will be readily appreciated that the blood drawing operation does not require any precise manipulation of the tube by the operator, and also eliminates the chance of injury resulting from tube breakage. Additionally, by using the cassette, there is no need for direct contact by the technician with the blood sampling tube so as to provide the dual advantages of protecting the technician from risk of injury from direct contact with the blood, and ensuring that the tube is adequately cleansed of blood. The size of the cassette allows for easy handling, and the surfaces of the cassette provide adequate space for attachment of labels and/or bar codes.

Since many changes and variations of the disclosed embodiment of the invention may be made without departing from the inventive concept, it is not intended to limit the invention otherwise than as required by the appended claims.

What is claimed is:

1. A cassette for holding a capillary tube during biological specimen sample drawing and analysis, said cassette comprising:

a) a body portion having a side wall, an open top end, and a closed bottom end;

b) a recess in said body portion sized to snugly receive a capillary tube through said open top end;

c) a lid for selectively closing one end of said recess, said lid including an elastomeric pad for pressing a capillary tube into said body portion recess when said lid closes said one end of said recess; and d) a transparency on said body portion for viewing a capillary tube disposed in said recess through said side wall to enable optical analysis of a sample in the capillary tube.

2. The cassette of claim 1 wherein said closure lid is hinged to one end wall of said body portion.

3. The cassette of claim 1 further comprising an absorbent gasket at one end of said recess for removing excess sample from an exterior surface of a capillary tube positioned in said recess.

4. The cassette of claim 1 wherein at least one of said side walls is disposed at an angle relative to said top and bottom walls so as to provide a dove tail engagement with a complimentary slot in a centrifuge platen.

5. An assembly for containing a biological fluid sample and analyzing the same, said assembly comprising:

a) a cassette comprising a body having opposed transparent side walls, top and bottom walls, and end walls, said cassette having an internal recess which opens through one of said end walls;

b) a sample-receiving transparent capillary tube disposed in said cassette recess, said capillary tube having one end thereof which projects a predetermined distance beyond said one of said cassette end walls sufficiently to allow drawing a specimen sample into said capillary tube via said projecting end thereof while said capillary tube is contained in said cassette; and c) said cassette having a closure lid which includes an elastomeric pad for pressing the capillary tube into said internal recess when said closure lid closes said cassette recess.

6. The assembly of claim 5 wherein said lid is hinged to one end wall of said body.

7. The assembly of claim 5 further comprising an absorbent gasket at one end of said recess for removing excess sample from an exterior surface of the capillary tube positioned in said recess.

8. The assembly of claim 5 wherein at least one of said side walls is disposed at an angle relative to said top and bottom walls so as to provide a dove tail engagement for the cassette with a complimentary slot in a centrifuge platen.

9. An assembly for containing a biological fluid sample wherein the sample can be gathered, centrifuged and subsequently analyzed in situ in the assembly, said assembly comprising:
   a) a transparent capillary tube, said capillary tube having an open ended cylindrical bore for receiving the fluid sample;
   b) a tubular cassette having a slotted or transparent side wall whereby said tube can be viewed when said tube is completely encased in said assembly, one closed end, and an opposite open end, said cassette having an internal recess which extends from said closed end to said open end;
   c) said capillary tube being positioned in said cassette recess with one end of said capillary tube projecting out of said cassette recess through said open end of said cassette;
   d) an elongated insert contained in said assembly, said insert being sized so as to be insertable in said tube bore for blood component layer elongation after the tube has been filled with sample, and the sample has been centrifuged in the assembly, said insert being located in said assembly initially at least partially externally of said tube bore; and
   e) a movable closure which is operable to close said open end of said cassette and to telescope said insert completely into said capillary tube bore during closure of said cassette after the capillary tube has been filled with sample.

10. An assembly for containing a biological fluid sample wherein the sample can be gathered, centrifuged and subsequently analyzed in situ in the assembly, said assembly comprising:
   a) a transparent tube, said tube having an open ended cylindrical bore for receiving the fluid sample;
   b) a tubular cassette having a slotted or transparent side wall whereby said tube can be viewed when said tube is completely encased in said assembly, one closed end, and an opposite open end, said cassette having an internal recess which extends from said closed end to said open end;
   c) said tube being positioned in said cassette recess with one end of said tube projecting out of said cassette recess through said open end of said cassette;
   d) an elongated insert contained in said assembly, said insert being sized so as to be insertable in said tube bore for blood component layer elongation after the tube has been filled with sample and the sample has been centrifuged in the assembly, said insert being located in said assembly initially at least partially externally of said tube bore; and
   e) a movable closure which is operable to close said open end of said cassette and to telescope said insert completely into said tube bore during closure of said cassette after the tube has been filled with sample.

11. An assembly for containing a biological fluid sample wherein the sample can be gathered, centrifuged and subsequently analyzed in situ in the assembly, said assembly comprising:
   a) a transparent tube, said tube having an open ended cylindrical bore for receiving the fluid sample;
   b) a tubular cassette having a slotted or transparent side wall whereby said tube can be viewed when said tube is completely encased in said assembly, one closed end, and an opposite open end, said cassette having an internal recess which extends from said closed end to said open end;
   c) said tube being positioned in said cassette recess with one end of said tube projecting out of said cassette recess through said open end of said cassette;
   d) an elongated insert contained in said assembly, said insert being sized so as to be insertable in said tube bore for blood component layer elongation after the tube has been filled with sample and the sample has been centrifuged in the assembly, said insert being located in said assembly initially at least partially externally of said tube bore; and
   e) a movable closure which is operable to close said open end of said cassette so as to encase said tube in said assembly.

12. An assembly for containing a biological fluid sample wherein the sample can be gathered, centrifuged and subsequently analyzed in situ in the assembly, said assembly comprising:
   a) a transparent tube, said tube having an open ended cylindrical bore for receiving the fluid sample;
   b) a tubular cassette having a slotted or transparent side wall whereby said tube can be viewed when said tube is completely encased in said assembly, one closed end, and an opposite open end, said cassette having an internal recess which extends from said closed end to said open end;
   c) said tube being positioned in said cassette recess with one end of said tube projecting out of said cassette recess through said open end of said cassette; and
   d) a movable closure which is operable to close said open end of said cassette so as to encase said tube in said assembly.

13. An assembly for containing a biological fluid sample wherein the sample can be gathered, centrifuged and subsequently analyzed in situ in the assembly, said assembly comprising:
   a) a transparent capillary tube, said tube having an open ended cylindrical bore for receiving the fluid sample;
   b) a tubular cassette having a slotted or transparent side wall whereby said capillary tube can be viewed when said capillary tube is completely encased in said assembly, one closed end, and an opposite open end, said cassette having an internal recess which extends from said closed end to said open end;
   c) said capillary tube being positioned in said cassette recess with one end of said capillary tube projecting out of said cassette recess through said open end of said cassette; and
   d) a movable closure which is operable to close said open end of said cassette so as to encase said capillary tube in said assembly.

* * * * *